(12) United States Patent
Knifong, Sr.

(10) Patent No.: US 8,612,015 B2
(45) Date of Patent: Dec. 17, 2013

(54) MOLDING DEVICE TO PRECISELY HOLD A RECHARGE ANTENNA

(71) Applicant: James Dan Knifong, Sr., Boulder, CO (US)

(72) Inventor: James Dan Knifong, Sr., Boulder, CO (US)

(*) Notice: Subject to any disclaimer, the term of this patent is extended or adjusted under 35 U.S.C. 154(b) by 0 days.

(21) Appl. No.: 13/799,811

(22) Filed: Mar. 13, 2013

(65) Prior Publication Data
US 2013/0253614 A1 Sep. 26, 2013

Related U.S. Application Data

(60) Provisional application No. 61/613,278, filed on Mar. 20, 2012, provisional application No. 61/658,235, filed on Jun. 11, 2012.

(51) Int. Cl.
*A61N 1/378* (2006.01)

(52) U.S. Cl.
USPC .................................................. 607/61

(58) Field of Classification Search
USPC .................................................. 607/61
See application file for complete search history.

(56) References Cited

U.S. PATENT DOCUMENTS

| | | | |
|---|---|---|---|
| 5,380,589 A | 1/1995 | Goodman et al. | |
| 7,738,965 B2 | 6/2010 | Phillips et al. | |
| 8,336,553 B2* | 12/2012 | Bhat et al. | 128/848 |
| 8,532,729 B2* | 9/2013 | Medina et al. | 600/344 |
| 2005/0075693 A1 | 4/2005 | Toy et al. | |
| 2005/0075694 A1 | 4/2005 | Schmeling et al. | |
| 2005/0075696 A1 | 4/2005 | Forsberg et al. | |
| 2005/0075697 A1 | 4/2005 | Olson et al. | |
| 2005/0075698 A1 | 4/2005 | Phillips et al. | |
| 2005/0075699 A1 | 4/2005 | Olson et al. | |
| 2005/0075700 A1 | 4/2005 | Schommer et al. | |
| 2005/0113887 A1 | 5/2005 | Bauhaun et al. | |
| 2005/0245996 A1 | 11/2005 | Phillips et al. | |
| 2009/0082835 A1 | 3/2009 | Jaax et al. | |
| 2009/0270951 A1 | 10/2009 | Kallmyer | |
| 2010/0241194 A1 | 9/2010 | Kast et al. | |

\* cited by examiner

*Primary Examiner* — Luther Behringer
(74) *Attorney, Agent, or Firm* — Patent Law Offices of Rick Martin, P.C.

(57) ABSTRACT

A method of making a custom mold and the custom mold itself having a first layer, a second layer, and a tail that are formed around the bulging area of an implantable medical device (IMD) are presented. The moldable material during hardening is flattened to form a docking platform for the flat planar bottom of an external antenna. The final apparatus of an antenna support may have all the custom contours of the patient's body around the implanted IMD. An optional tape patch and/or bandage may help maintain a proper placement of the external antenna over the IMD depending on amount of mobility the patient wishes to have during charging. An alternate embodiment uses magnets to secure an external antenna over a metallic segment of an IMD.

15 Claims, 17 Drawing Sheets

MOLDING DEVICE TO PRECISELY HOLD A RECHARGE ANTENNA

CROSS-REFERENCE TO RELATED APPLICATIONS

This application claims benefit under 35 USC 119(e) of provisional applications No. 61/613,278 filed Mar. 20, 2012 and 61/658,235 filed Jun. 11, 2012 of common inventorship.

FIELD OF INVENTION

The present invention relates to stabilizing a recharge antenna with respect to a rechargeable implanted medical device (RIMD) by use of a custom body mold.

BACKGROUND OF THE INVENTION

Implantable medical devices (IMD) for producing a therapeutic result in a patient are well known. An example of such an IMD includes implantable neurostimulators used for the treatment of movement disorders such as Parkinson's disease, essential tremor, and dystonia. Other examples of such IMDs include implantable drug infusion pumps, implantable cardioverters, implantable cardiac pacemakers, implantable defibrillators, and cochlear implants. It is recognized that other IMDs are envisioned that utilize energy delivered or transferred from an external device.

A common element in all of these IMDs is the need for electrical power in the IMD. The IMD requires electrical power to perform its therapeutic function whether it be driving an electrical infusion pump, providing an electrical neurostimulation pulse, or providing an electrical cardiac stimulation pulse. This electrical power is derived from a power source.

Typically, a power source for an IMD can take one of two forms. The first form utilizes an external power source that delivers the energy via wires or radio frequency energy. Having electrical wires that perforate the skin is disadvantageous due, in part, to the risk of infection. Further, continuously coupling patients to an external power for therapy is, at least, a large inconvenience. The second form utilizes batteries as the source of energy of the implantable medical device. This can be effective for low power applications, such as pacing devices. However, such batteries usually do not supply the lasting power required to perform new therapies in newer IMDs. In some cases, such as an implantable artificial heart, a battery might last the patient only a few hours. In other, less extreme cases, a single cell unit might expel all or nearly all of its energy in less than a year. This is not desirable due to the need for surgery to explant and re-implant the IMD or replace a portion of the device, such as the battery. One solution is for electrical power to be transcutaneously transferred through the use of inductive coupling. Such electrical power or energy can optionally be stored in a rechargeable battery. In this form, an internal power source, such as a battery, can be used for direct electrical power to the IMD. When the battery has expended, or nearly expended, its capacity, the battery can be recharged transcutaneously, via inductive coupling from an external antenna temporarily positioned on the surface of the skin and an external power source. Several systems and methods have been used for transcutaneous inductive recharging a rechargeable battery in an IMD.

Transcutaneous energy transfer through the use of inductive coupling involves the placement of two coils positioned in close proximity to each other on opposite sides of the cutaneous boundary. The internal coil, or secondary coil, is part of or otherwise electrically associated with the IMD. The external coil, or primary coil, is associated with the external power source or external charger or recharger. The primary coil is driven with an alternating current. A current is induced in the secondary coil through inductive coupling. The current can then be used to power the implanted medical device or to charge or recharge an internal power source or a combination of the two.

For RIMDs, the efficiency at which energy is transcutaneously transferred may be crucial. First, the inductive coupling, while inducing a current in the secondary coil, also has a tendency to heat surrounding components and tissue. The amount of heating of surrounding tissue, if excessive, can be deleterious. Since heating of surrounding tissue is limited, so also is the amount of energy transfer that can be accomplished per unit time. The higher the efficiency of energy transfer, the more energy can be transferred while at the same time limiting the heating of surrounding components and tissue. Second, it is desirable to limit the amount of time required to achieve a desired charge, or recharge, of an internal power source. While charging or recharging is occurring, the patient necessarily has an external encumbrance attached to his or her body. This attachment may impair the patient's mobility and limit the patient's comfort. The higher the efficiency of the energy transfer system, the faster the desired charging or recharging can be accomplished thus limiting any inconvenience to the patient. Third, the amount of charging or recharging can be limited by the amount of time required for charging or recharging. Since the patient is typically inconvenienced during such charging or recharging, there is a practical limit on the amount of time during which charging or recharging should occur. Hence, the size of the internal power source can be limited by the amount of energy that can be transferred within the amount of charging time. It is evident that, the higher the efficiency of the energy transfer system, the greater amount of energy that can be transferred, and hence, the greater the practical size of the internal power source. This allows the use of implantable medical devices having higher power use requirements and providing greater therapeutic advantage to the patient and/or extends the time between charging effectively increasing patient comfort.

The problems with the external charging systems are that the external antenna must be aligned precisely with the implanted medical device in order to charge efficiently. For most external charging systems there is a connected LED display that communicates the charge rate so that the user may optimally position the external antenna. This process must be repeated each time the implanted device needs to be charged. Further once an optimal charging position is achieved it is hard to maintain this due to body movements. Even when the user is lying still, natural breathing movements may dislodge the external antenna from its optimum position. At present the available LED displays for the external charging systems do not warn a patient that optimal charging is not taking place. The patient must maintain visual contact with the display to make sure the device is continuing to charge optimally. What is needed in the art is a better system for maintaining the optimal position of the external antenna and better feedback for the user if the charger is not performing optimally.

U.S. Pat. No. 7,738,965 has attempted to address this issue with a holster that fits around the chest or waist of the user somewhat like a Sam Brown belt. A Sam Brown belt being a wide belt, which is supported by a strap passing diagonally over the right shoulder. This holster allows for a clip-on holder for an external charging device and contains a pocket that holds the antenna, one strap fits around the chest or waist while another goes over the shoulder. This holster is claimed by the inventors to be effective while the user is sitting upright in a chair performing tasks such as typing or writing. The present inventor has tested this device and found that this is not the case.

Therefore, need still exists for an apparatus and method for stabilizing an external antenna in an optimum position so as to limit amount of time needed to charge an implanted medical device. Optimally this apparatus would allow some level of activity during the charge so that the user is not substantially inconvenienced.

The present invention solves the problem of stabilizing an external antenna of the charger in the optimal position to recharge an implanted medical device by providing a unique molded cast to hold the external antenna and method of making this unique molded cast.

SUMMARY OF THE INVENTION

The main aspect of the present invention is to provide a process to form a custom body cast which supports an external charging coil or antenna against the human skin which covers the surface of the internal coil of a Rechargeable Implantable Medical Device (RIMD), and does so in the optimum position.

Another aspect of the present invention is to utilize a two-sided tape segment to further stabilize the internal-to-external coil surface contact.

Another aspect of the present invention is to utilize an elastic bandage to help secure the custom mold and external antenna against the RIMD.

Another aspect of the present invention is to utilize an elastic holster to help secure the custom mold and external antenna against the RIMD.

Another aspect of the present invention is to form a custom RIMD with metal ears to attract an external antenna housing with matching magnets which may be rare earth magnets.

Currently the RIMD patient must maneuver the external antenna(s) to the point, and orientation, on the body for a suitable transmission rate between the external antenna and the internal receiver (as indicated by the external metering device). The external antenna(s) must then be held in this precise position during the charging period, which can take from a few minutes to a few hours, depending on the charging rate and the charge state of the internal battery. Stabilizing the antenna(s) on the patient's body in the optimum position with a mold allows the patient to 1) immediately find that position on subsequent charging sessions, 2) easily hold the antenna(s) in optimum position, and 3) reduce charging time to a minimum.

A molding material is defined herein as any semi-solid that hardens into a solid or an elastic solid. Some of these moldable materials are historically or presently used in the dental field for making impressions of the teeth. Examples of molding material include, but are not limited to, plaster of Paris, zinc oxide eugenol, agar, as well as the new two-part, rubber-like silicones that set up very quickly and remain pliable and soft. These new two-part materials may include sodium alginate, polyether and silicones, both condensation-cured silicones and addition-cured silicones, such as polyvinyl siloxane.

One moldable material tried by the inventor was plaster of Paris. A readily available modling putty, called Amazing Mold Putty (http://amazingmoldputty.com/), was also tried. A third type of material tried was a dental impression product. The Aquasil Ultra Regular Set Monophase product from Dentsply International (http://dentsply.ca/) and Examix from GC America Inc. (http://www.gcamerica.com/index.php) were used with equally good results. The Aquasil Ultra Monophase product is covered by U.S. Pat. No. 5,661,222 and No. 5,863,965 as well as other pending applications. These silicone and vinyl polysiloxane products produced an accurate mold that set in approximately five minutes. Product directions were followed and 2-3 product cartridges were used to produce the final product.

It is envisioned that other comparable products could be used to produce molds similar to what have been produced here. Moldable material such as caulk used in construction settings are but one example.

The body mold of the present invention can be extensive, covering a large area, as when the internal part is deep in the abdomen, or minimal as when the internal part is near the surface and its shape is sharply defined though the skin. The molding of the body and the antenna can be done in one cast, or two or more, keyed together molds, depending on the position of the internal antenna on the body. If necessary, and desirable, once the external antenna is positioned in its cured mold and the mold is positioned in its proper place on the body, the whole apparatus can be held in place with an elastic bandage, elastic fabric straps, or elastic harness. The antenna can also be secured in place with two-sided, easy-release tape such as artists use, or any of a variety of gum adhesives. The applicants have used "Scotch"® Restickable tabs (http://www.scotchbrand.com/wps/portal/3M/en_US/ScotchBrand/Scotch/). The external antenna support may have an optional "tail" mold feature as depending on region of implantation this may not be needed. This tail may aid in stabilizing the external antenna in the desired location. For example the device presented below is designed around a protruding implantable device located just below the collar bone in the pectoral area. Having a tail that anchors to the indent in the collar bone stabilizes the mold and holds the antenna in a more stable position. For the case where the implanted device may be located behind the ear a tail may be formed over the ear to stabilize the charging unit. When the implantable device is located in the middle region of the body such as in the abdomen or lower back a mold may need further stabilization with the adhesive tape, elasticized bandage, straps, or harness. The internal catheter may also serve as a site for anchoring the mold.

Various patient activity levels may be maintained during the charging process. The table below summarizes these levels and the success of using the current invention and prior art invention at different activity levels. The prior art device and method of charging is that presented by Phillips et al. in U.S. Pat. No. 7,738,965, hereafter ('965), and is a holster that is made to receive the external antenna unit and has two straps, the first fitting around the torso and the second extending up over one shoulder and coming down to attach to the first strap. These straps are tightened via shortening or lengthening of the strap using an adjuster. Although the patent recites that the holster may be made from elastic material the design sold by Phillips is not elastic. The '965 device will stabilize the antenna during activities such as moderate household chores corresponding to activity levels II-VI in Table 1 below, these results could not be duplicated by our test subject. The angle of recline of the patient is also given. This angle is that measured from a seated or standing position such that at a 0° angle is seating with back straight up, +90° angle is would be leaning forward such that the torso is parallel with the ground with the front facing the ground, and a −90° is leaning backwards such that the torso is parallel with the ground with the back facing the ground.

TABLE 1

| Level | Activity | Success using present invention | Success using prior art invention (U.S. Pat. No. 7,738,965) | % of Incline |
|---|---|---|---|---|
| I | Vigorous sport: tennis, running, cycling | Nearly impossible to keep external antenna positioned by any means. Not a practical goal. | Holster not efficient at this activity level. | Varies +45° to −20° |
| II | Moderate household movement: light cleaning, cooking, entertaining friends | Possible to keep external antenna positioned with elastic bandage & mold. | Holster not efficient at this activity level. | Varies +45° to −20° |
| III | Desk work: sitting upright with occasional movement | Easy to keep external antenna positioned with elastic bandage & mold. | Holster not efficient at this activity level. | Varies +20° to −20° |
| IV | Seated in reclining chair, reading, watching television, using a laptop computer with little upper body movement | Mold holds external antenna stable, efficiently charges with no extra manipulation needed. | Holster not efficient at this activity level. | −20° to −40° |
| V | Sitting in a reclining chair with no upper body movement | Mold holds external antenna, efficiently charges with no extra manipulation needed. | Holster not efficient at this activity level. | −30° to −70° |
| VI | Lying prone | Difficult because of the likelihood of falling asleep and accidentally moving the antenna. | Holster not efficient at this activity level. | −70° to −90° |

Another way to establish and hold the position is with magnets. Most IMD are made as compact as possible and encased in titanium, a non-magnetic metal. This titanium case typically holds non-magnetic elements: copper, gold, silicone. By adding either iron or one of the rare earth magnetic materials, such as neodymium, to specific positions in the encasement (See FIG. 15), corresponding points of rare-earth magnets can be added to the external antenna (See FIG. 16) thus assuring attraction/holding points through the skin. By using soft iron in the internal titanium case and various strength magnets in individual accessible pockets on the external antenna, the attraction can be externally adjusted so there is sufficient attraction to position and hold the antenna, and not so much as to pinch and damage the skin, regardless of how thick or thin it may be on an individual patient. Although FIGS. 15 and 16 show only two points of attraction, one would be sufficient if used with another positioning method and three or more might be desirable.

Other aspects of this invention will appear from the following description and appended claims, reference being made to the accompanying drawings forming a part of this specification wherein, like reference characters, designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE DRAWINGS

The term "charge" refers to any type of charge including, but not limited to, an initial charge and a recharge. The pectoral region is preferably proximate the pectoral muscles and is more preferably within a region of the body below the clavicle, above the xiphoid process of the sternum, and between the sternum and the axilla, which is a cavity beneath the junction of the arm and the torso. An example of a suitable pectorally implanted medical device for use with the present invention is disclosed in U.S. Patent Publication No. US 2005/0245996 A1, published Nov. 3, 2005, entitled Spacers for Use with Transcutaneous Energy Transfer System.

Figure 1:
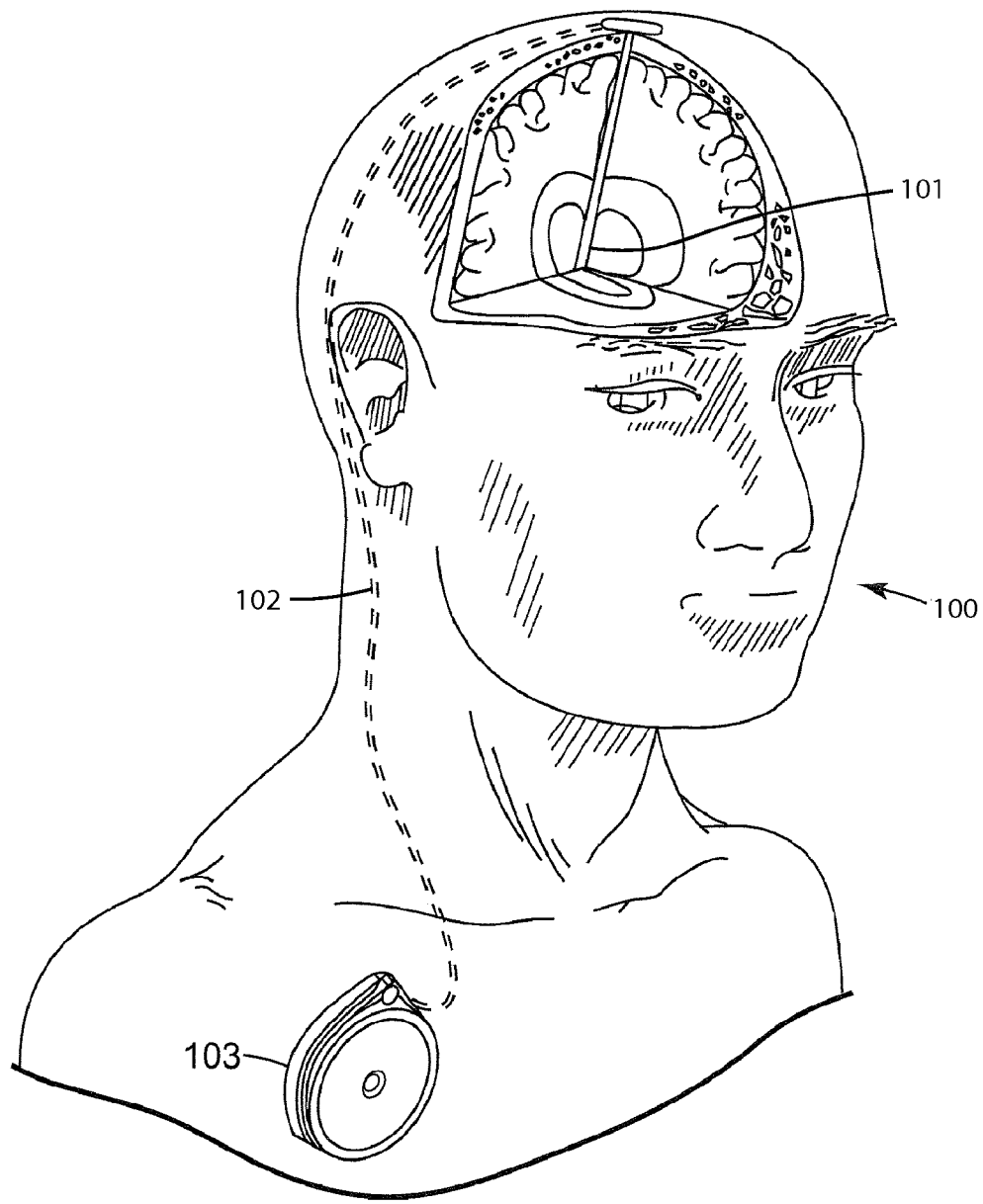
FIG. 1 (prior art) is an illustration of an RIMD implanted in a patient.

FIG. 1 shows a pectorally implanted medical device 103, for example a neurostimulator used for the treatment of a movement disorder such as Parkinson's disease, essential tremor, and dystonia, implanted in the pectoral region of a patient 100. The pectorally implanted medical device 103 is typically implanted by a surgeon in a sterile surgical procedure performed under local, regional, or general anesthesia. During the sterile surgical procedure, a catheter 102 is typically implanted with the distal end position at a desired therapeutic delivery site 101 and the proximal end tunneled under the skin to the location where the pectorally implanted medical device 103 is to be implanted.

Figure 2:
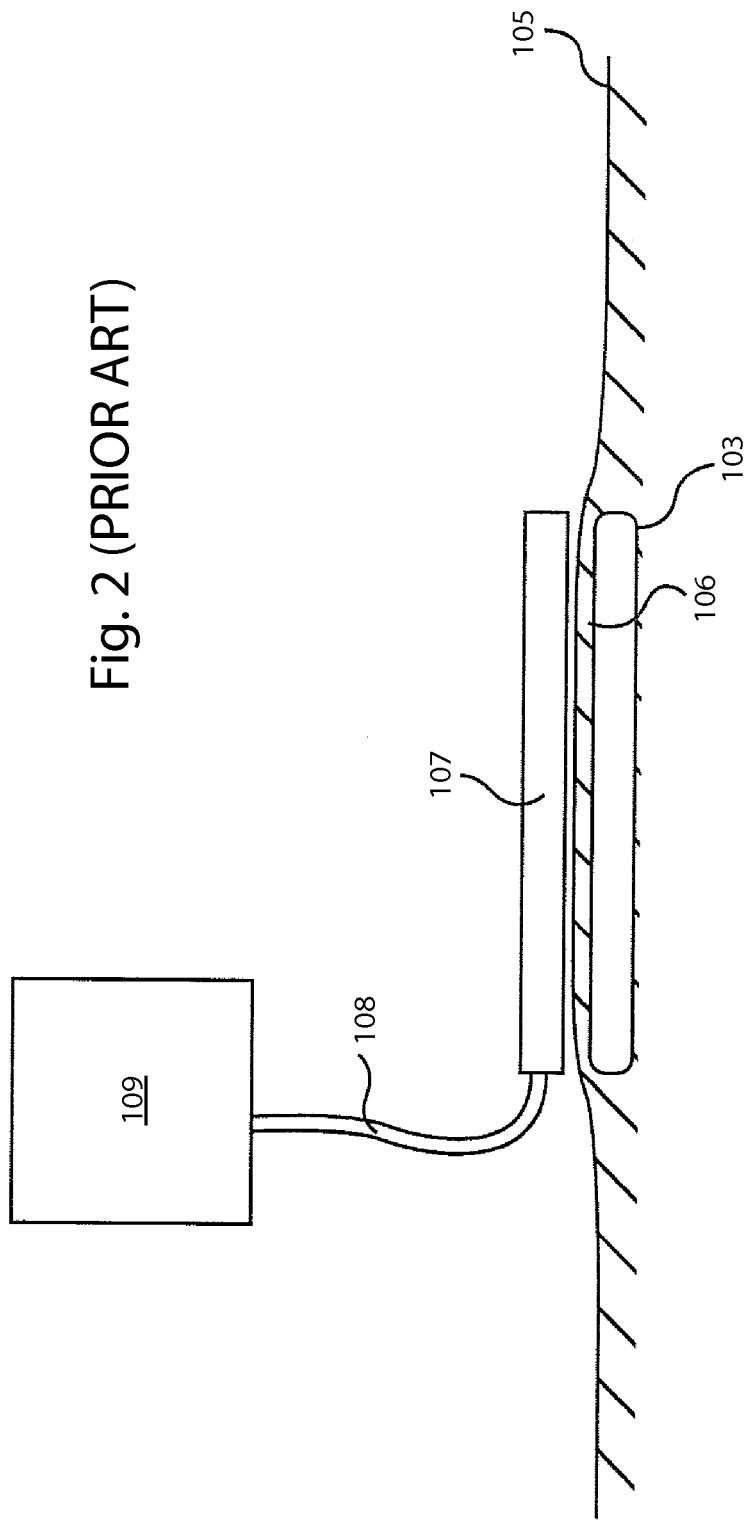
FIG. 2 (prior art) is a schematic cross-sectional side view of an external antenna and an RIMD implanted in a patient.
Figure 3:
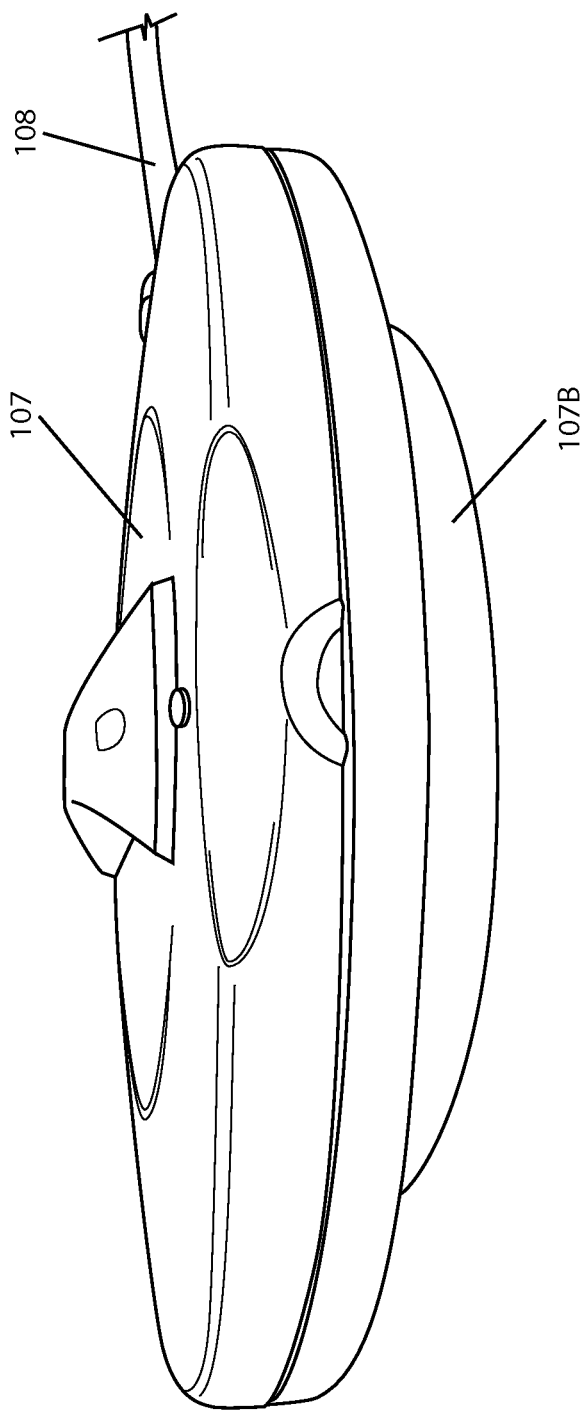
FIG. 3 (prior art) is a side perspective view of an external antenna.
Figure 4:
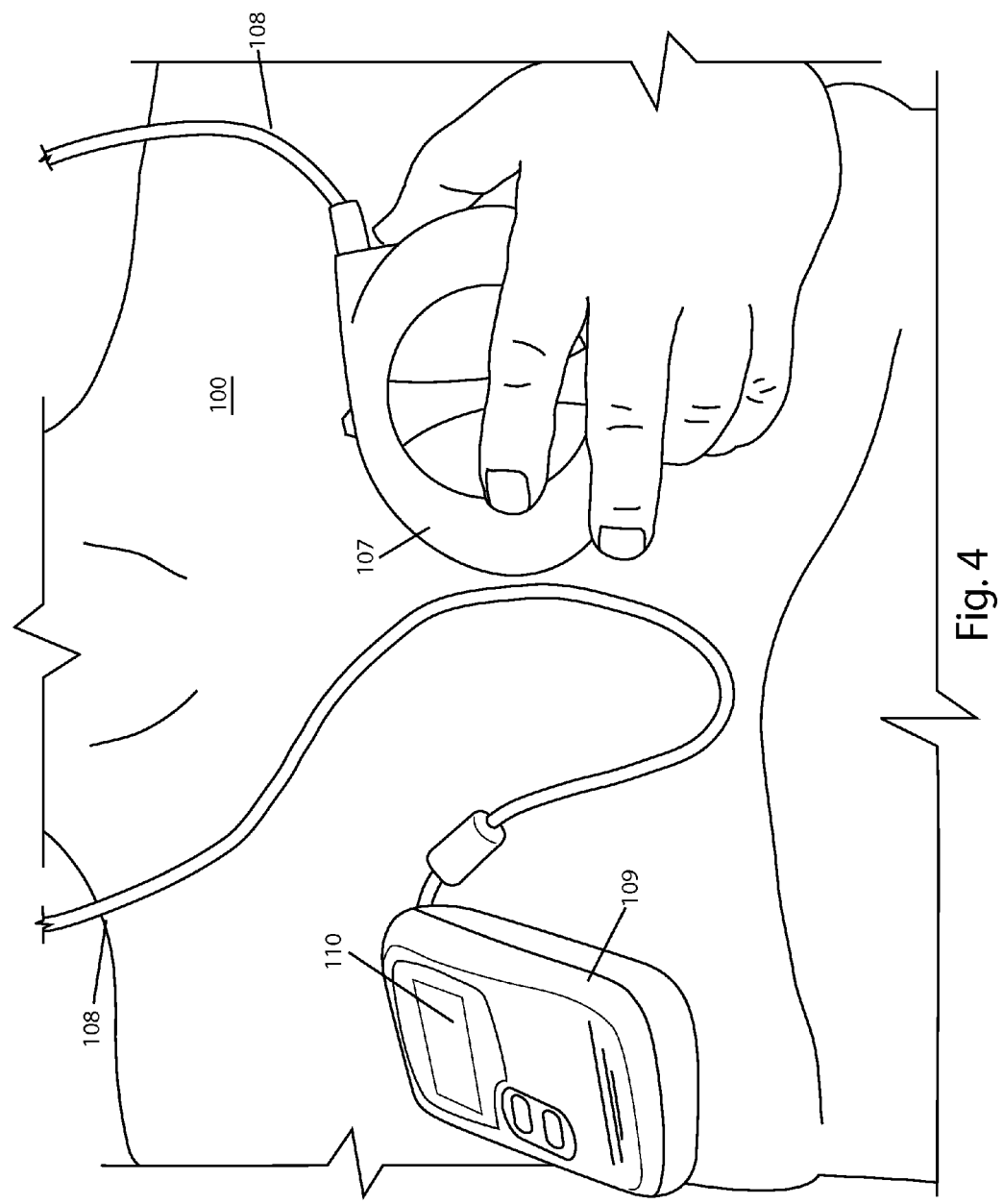
FIG. 4 (prior art) is front perspective view of a patient manually holding the external antenna against his RIMD.

As shown in FIGS. 2, 3, and 4, the RIMD 103 can be implanted pectorally. Once the pectorally implanted medical device 103 is implanted into the patient 100, the incision can be sutured closed, and the pectorally implanted medical device 103 can begin operation. The implanted medical device 103 can be any suitable RIMD such as, but not limited to, implantable neurostimulators, implantable drug infusion pumps, implantable cardioverters, implantable cardiac pacemakers, implantable defibrillators, and cochlear implants. The pectorally implanted medical device 103 includes a rechargeable power source that can be charged while the pectorally implanted medical device 103 is implanted in a patient through the use of an external charging device comprising an external antenna 107 and a charging unit 109. The charging unit 109 may also be referred to as a recharger. The charging unit 109 contains the electronics necessary to drive a primary coil in the antenna 107 with an oscillating current in order to induce a current in a secondary coil in the pectorally implanted medical device 103 when the primary coil in the antenna 107 is placed in proximity of the secondary coil in the pectorally implanted medical device 103. The charging unit 109 is operatively coupled to the primary coil in the antenna 107 by cable 108. Suitable charging units include without limitation those described in U.S. Patent Publication Nos. 2005/0113887; 2005/0075700; 2005/0075699; 2005/0075698; 2005/0075697; 2005/0075696; 2005/0075694; and 2005/0075693; all of which are incorporated herein by reference.

As shown in FIG. 2, the pectorallly implanted medical device 103, when implanted, usually leaves an area of the patient's body that is not quite as flat as it was before implantation. That is, the pectorally implanted medical device 103 usually leaves a bulging area 106 proximate to the surface of the patient's skin which bulges outward somewhat to accommodate the bulk of the pectorally implanted medical device 103. It is typically relatively easy for the patient, the medical professional, or another person to place the antenna 107 in the general area of the pectorally implanted medical device 103 and move the antenna 107 around until the antenna 107 is relatively centered with the bulging area 106. Once the antenna 107 is positioned optimally in this manner, the antenna 107 can be secured to the patient's body.

As shown in FIG. 2, a schematic cross-sectional side view of an antenna 107 and a pectorally implanted medical device 103 implanted subcutaneously in the pectoral region of a patient, the pectorally implanted medical device 103 is implanted in a patient under cutaneous boundary 105 creating bulging area 106, an area of the patient's body in which the patient's skin is caused to bulge slightly due to the implantation of the pectorally implanted medical device 103. Bulging area 106 is an aid to locate the position of the secondary coil in the pectorally implanted medical device 103 and the antenna 107 can be positioned proximate the area where the pectorally implanted medical device 103 is implanted. The antenna 107 is placed over the bulging area 106 to charge the pectorally implanted medical device 103. Depending upon the application and the pectorally implanted medical device 103, the pectorally implanted medical device 103 is generally implanted subcutaneously at depths of from 1 centimeter (0.4 inches) to 2.5 centimeters (1 inch) where there is sufficient tissue to support the implanted system. However, the locations of the implantation vary from patient to patient. The amount of bone and the amount of soft tissue between the bone and the cutaneous boundary 105 are factors that affect the actual depth of implant. The actual depth of the implant, as well as the amount of soft tissue at, and around, the implant site, affect the size and shape of bulging area 106 at the implant site. Further, the location of the pectorally implanted medical device may vary in the patient due to any movement of the pectorally implanted medical device, especially if the pectorally implanted medical device is not sutured into place, any weight loss or gain, or any loss or gain of muscle mass.

This type of a transcutaneous energy transfer system can be utilized over extended periods of time, either to power the pectorally implanted medical device 103 over an extended period of time or to charge a replenishable power supply within the pectorally implanted medical device 103. Depending upon the capacity of the replenishable power supply and the efficiency of the energy transfer, the charging unit 109 and the antenna 107 can be utilized for hours. Further, over the extended period of time in which the charging unit 109 is utilized, antenna 107 is affixed to the patient's body. As the patient attempts to continue a normal routine, such as by making normal movement or by sleeping, during the energy transfer, it may be difficult to maintain the antenna 107 in a fixed position relative to the secondary coil in the pectorally implanted medical device 103. Movement of the antenna 107 with respect to the secondary coil can result in a change in mutual inductance, L mutual' a change in impedance, and a change in the resonant frequency, fresonate. Further, any change in spatial positioning of the energy transfer system with any external conductive object, any change in the characteristics of the antenna 107, such as by fractures in the magnetic core, for example, a change in the charge level of the rechargeable power source of the pectorally implanted medical device 103 or a change in the power level of the charging unit 109, any of which can result in a change of mutual inductance, L mutual'. The pectoral region of the patient is typically not a flat surface so the antenna 107 may not sit in the optimal position against the patient's skin. This may be especially true as the patient moves and the pectoral region moves during such movement.

Referring next to FIG. 3 the external antenna 107 is shown to have a flat bottom 107B for contact with the bulging area 106 shown in FIG. 2. The cable 108 is shown.

Referring next to FIG. 4 the prior art method of charging using the charging unit 109 is shown. The patient tries to hold the flat bottom 107B (covered in FIG. 4) of the external antenna 107 against his bulging area 106 (covered in FIG. 4) to maximize the charge shown on the screen 110 of the charging unit 109.

Figure 5:
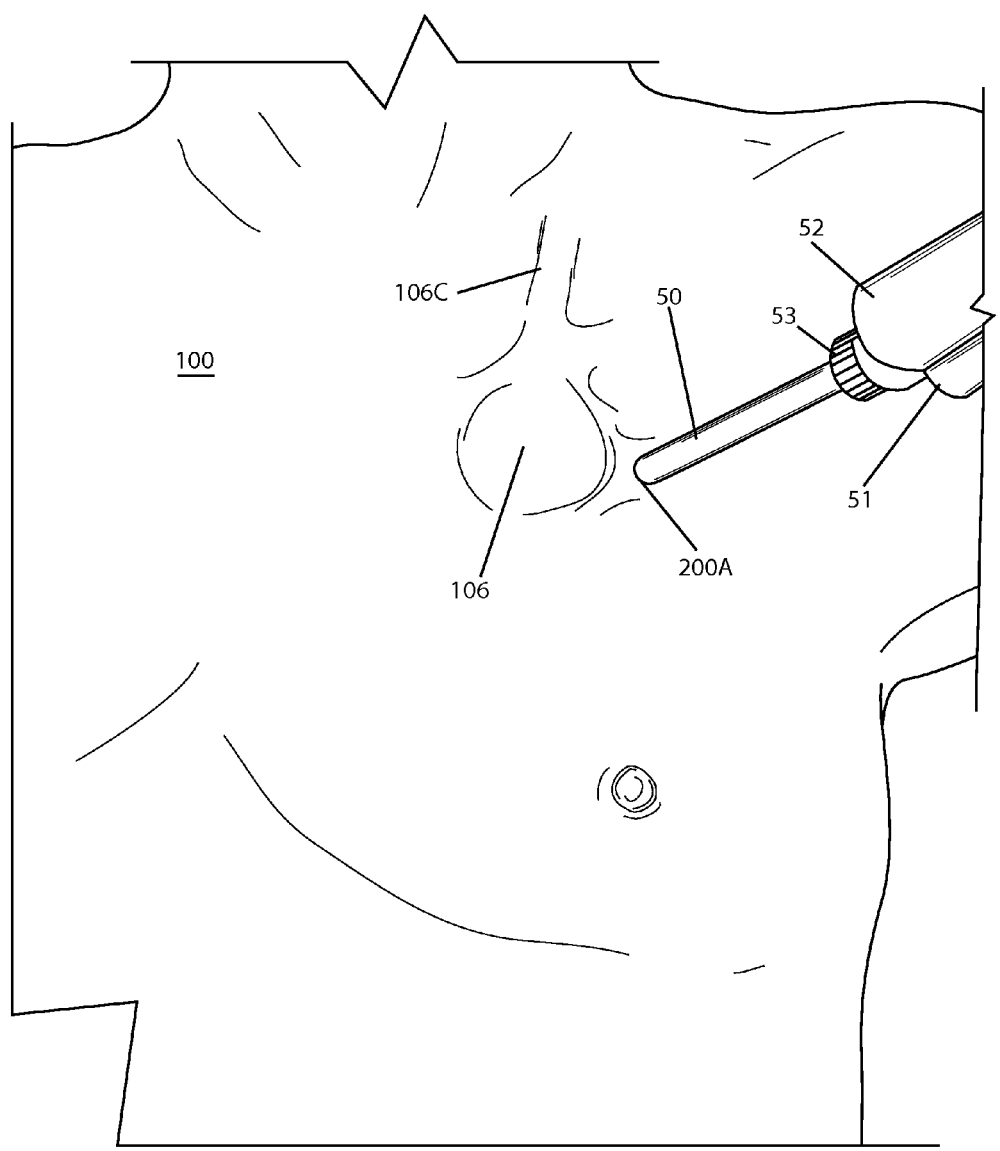
FIG. 5 is a front elevation view of a patient starting to apply the moldable material around the RIMD.

Referring next to FIG. 5 a two part material applicator 53 has tubes 51 and 52 combining in applicator tip 50. Step one of the present invention is to apply the moldable material 200A around the bulging area 106 of the patient 100. As discussed above the Aquasil Ultra Monophase product from Dentsply and ExaMix from GC America are examples of moldable material products used for the present invention.

Figure 6:
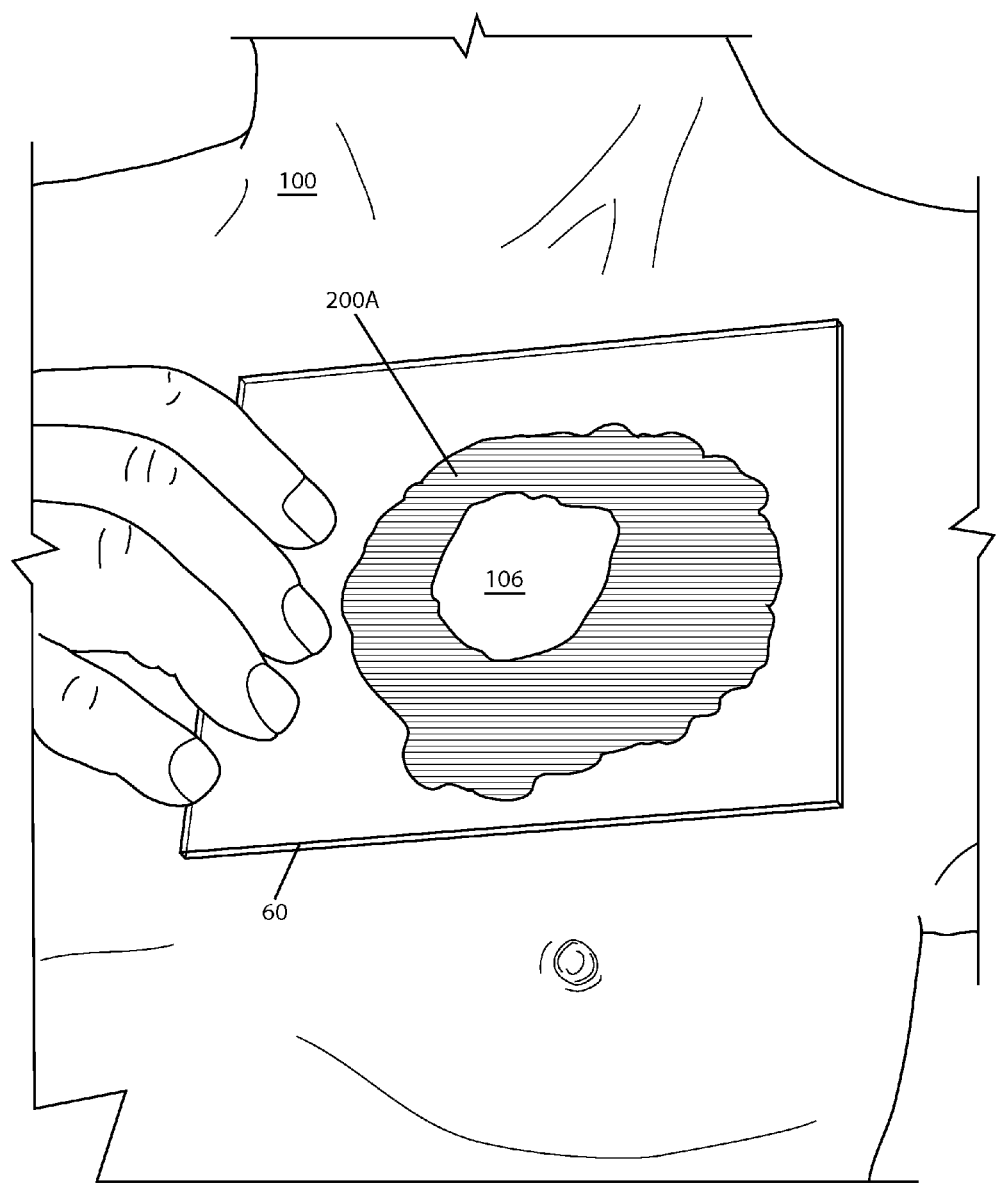
FIG. 6 is a front elevation view of a patient compressing flat the moldable material.

Referring next to FIG. 6, step two is shown wherein the moldable material 200A has been applied all around the bulging area 106. And a flat plate 60 has compressed the circle of moldable material 200A against the patient 100. The material is allowed to set for a period of about five minutes. A flat top planar surface has now been formed on the moldable material 200A. A hole has been formed in the moldable material 200A by application of the material around but not over the bulging area 106. The bottom of the external antenna 107B will rest on the flat top planar surface formed by the flat plate and press against the patient's bulging area 106 which is exposed.

Figure 7:
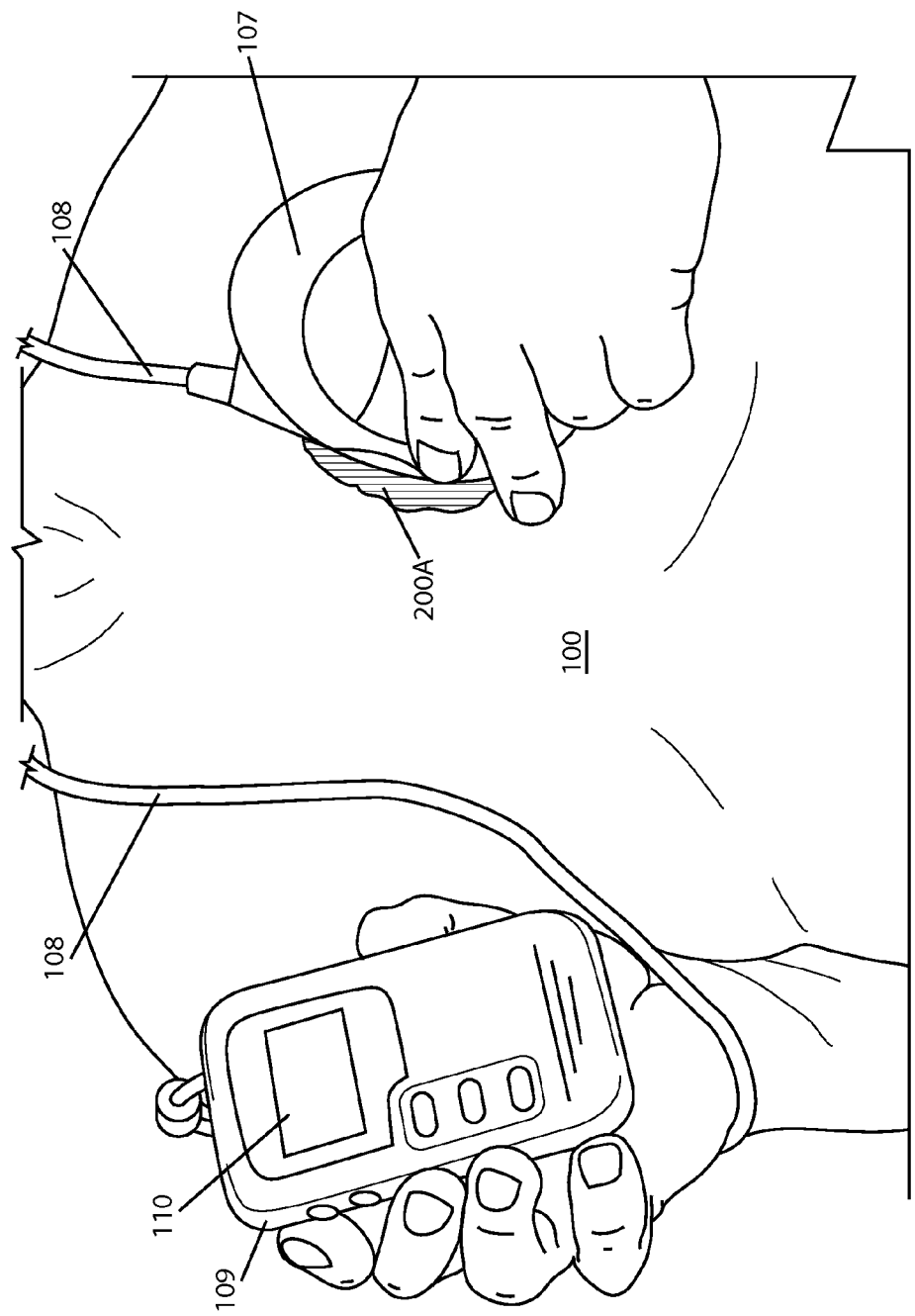
FIG. 7 is a front elevation view of the patient checking the charging strength while holding the external antenna against a newly hardened mold.

Referring next to FIG. 7, the patient is testing the position between the bottom of the external antenna 107B (hidden) and the exposed bulging area 106 (hidden) while the external antenna 107 is held on the first layer of moldable material formed 200A. This is step three wherein the charging unit 109 is used to find an optimal charging position.

Figure 8:
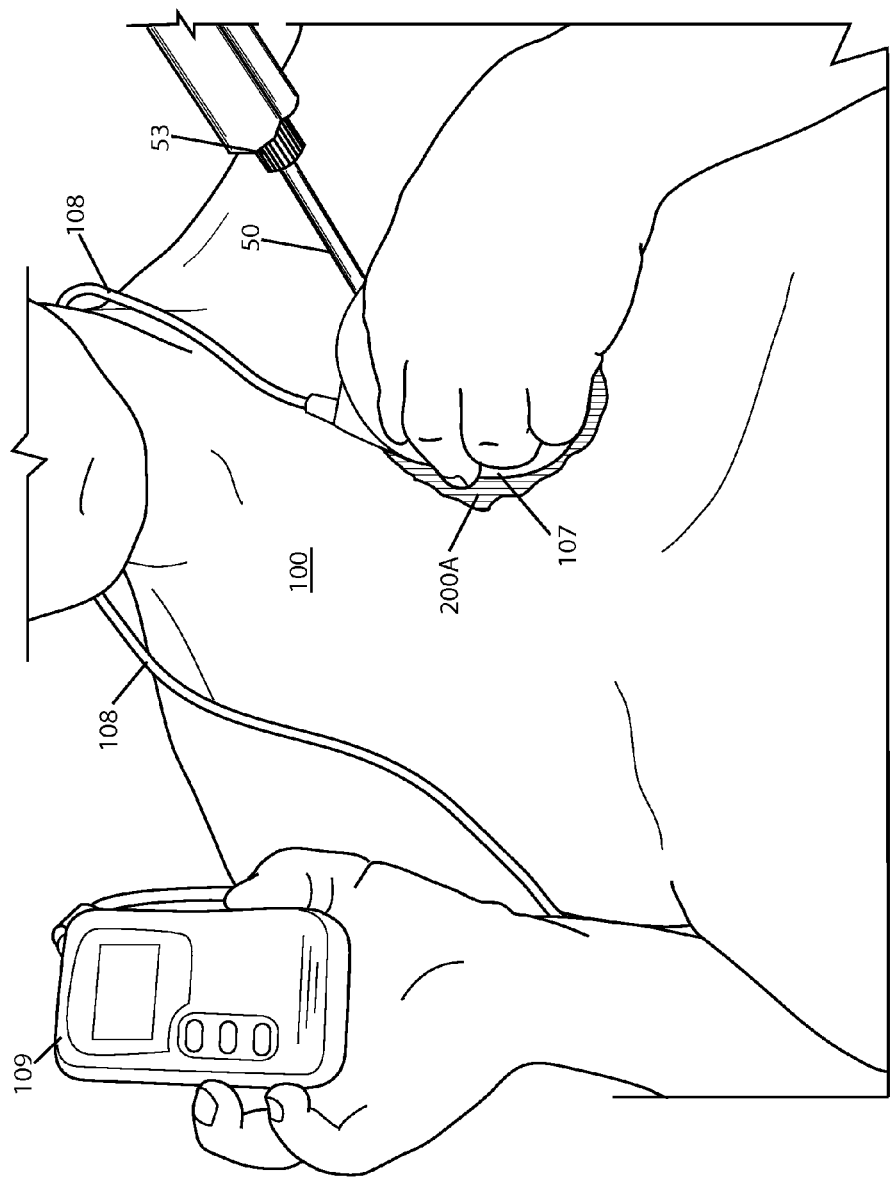
FIG. 8 is a front elevation view of the start of the second phase of forming a mold.
Figure 9:
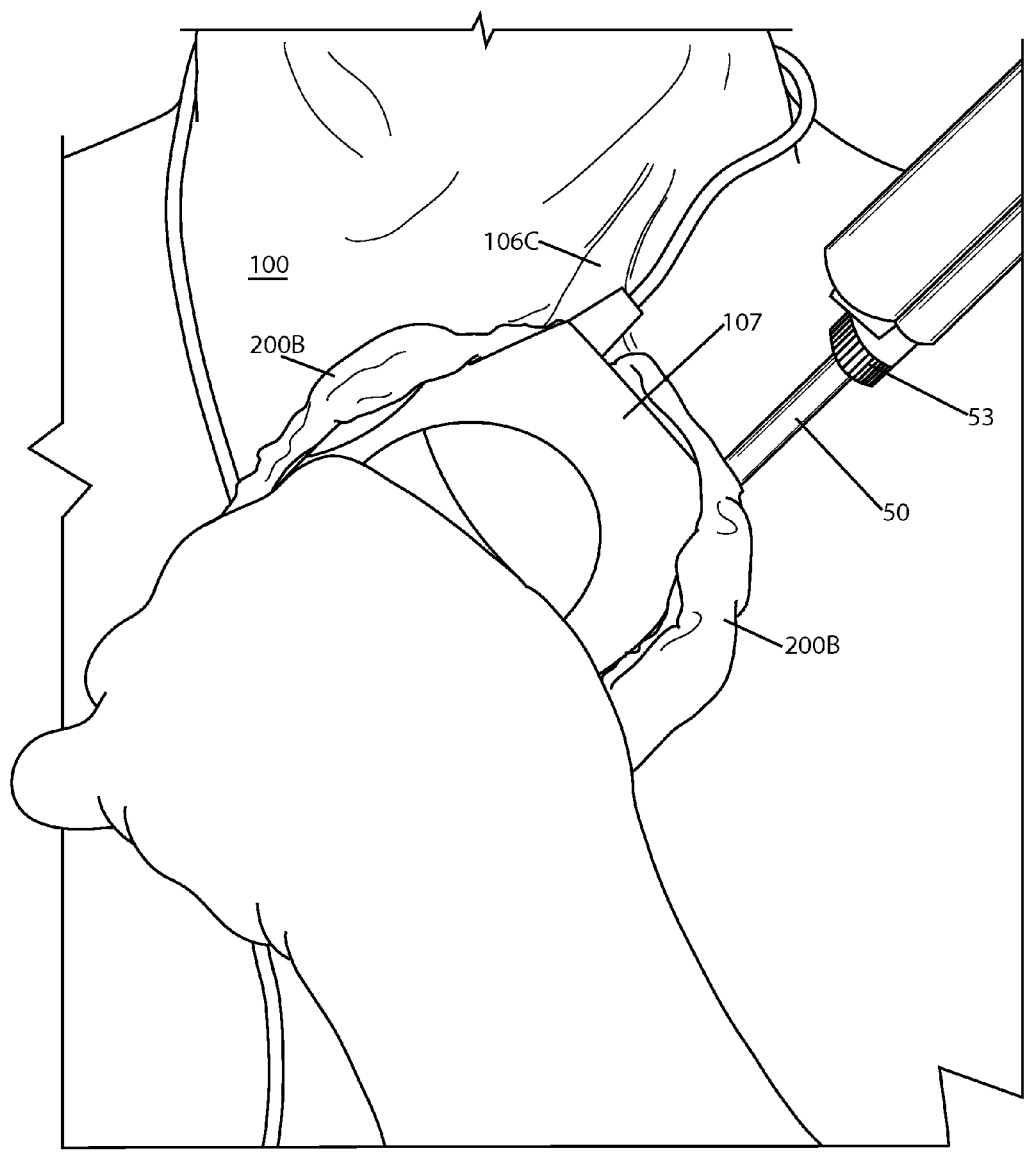
FIG. 9 is front elevation view of half-way through the second phase of forming a mold.

Referring next to FIG. 8, step four is shown wherein a second layer of moldable material 200B is applied by the applicator tip 50 to contact with the first layer of moldable material 200A. The moldable material 200B is applied around the side edges of the external antenna 107 while it is held in the optimal charging position located in step three. Referring next to FIG. 9, step four is completed forming a second layer of moldable material designated 200B.

Figure 10:
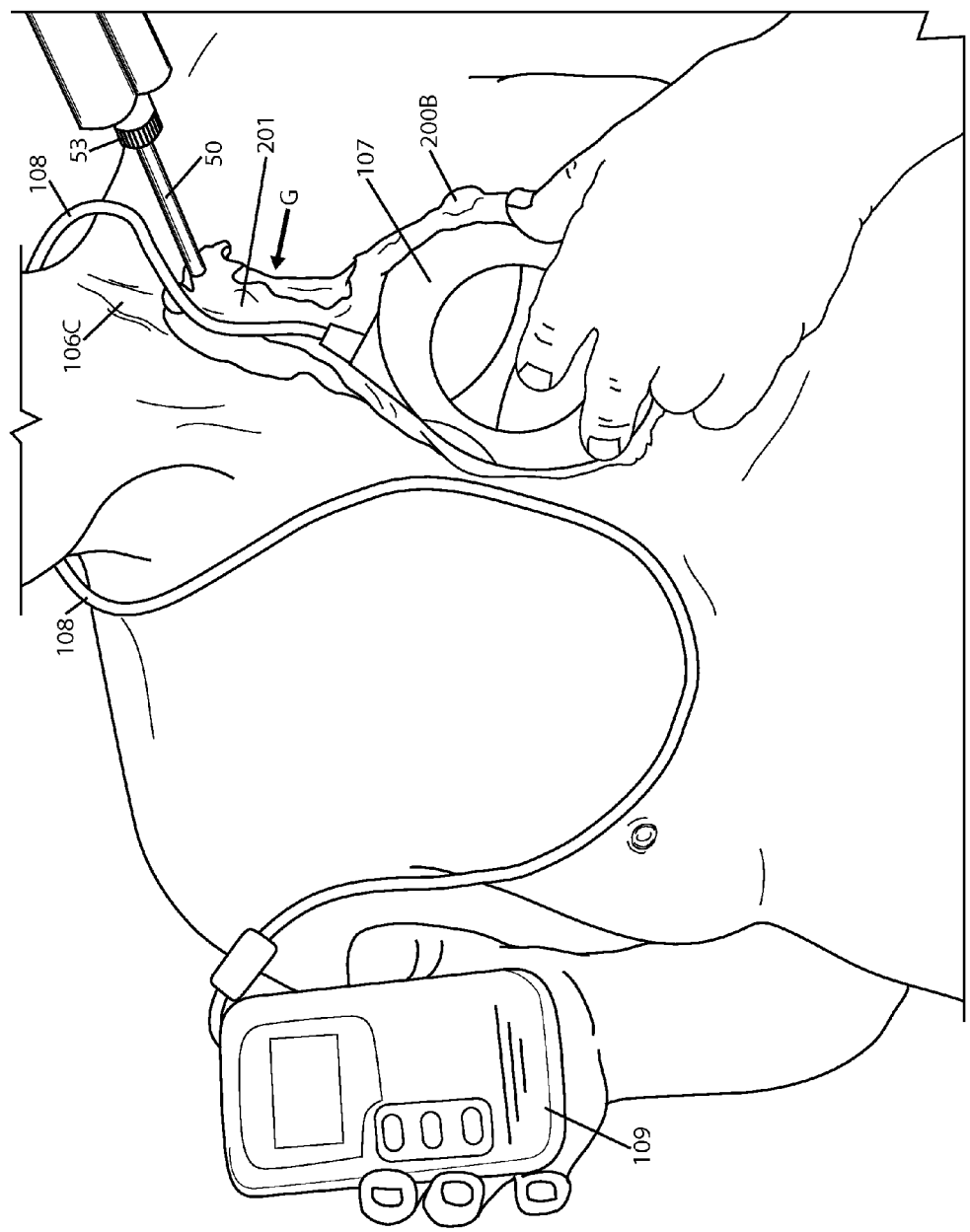
FIG. 10 is a front elevation view of completing the second phase of forming a mold.
Figure 11:
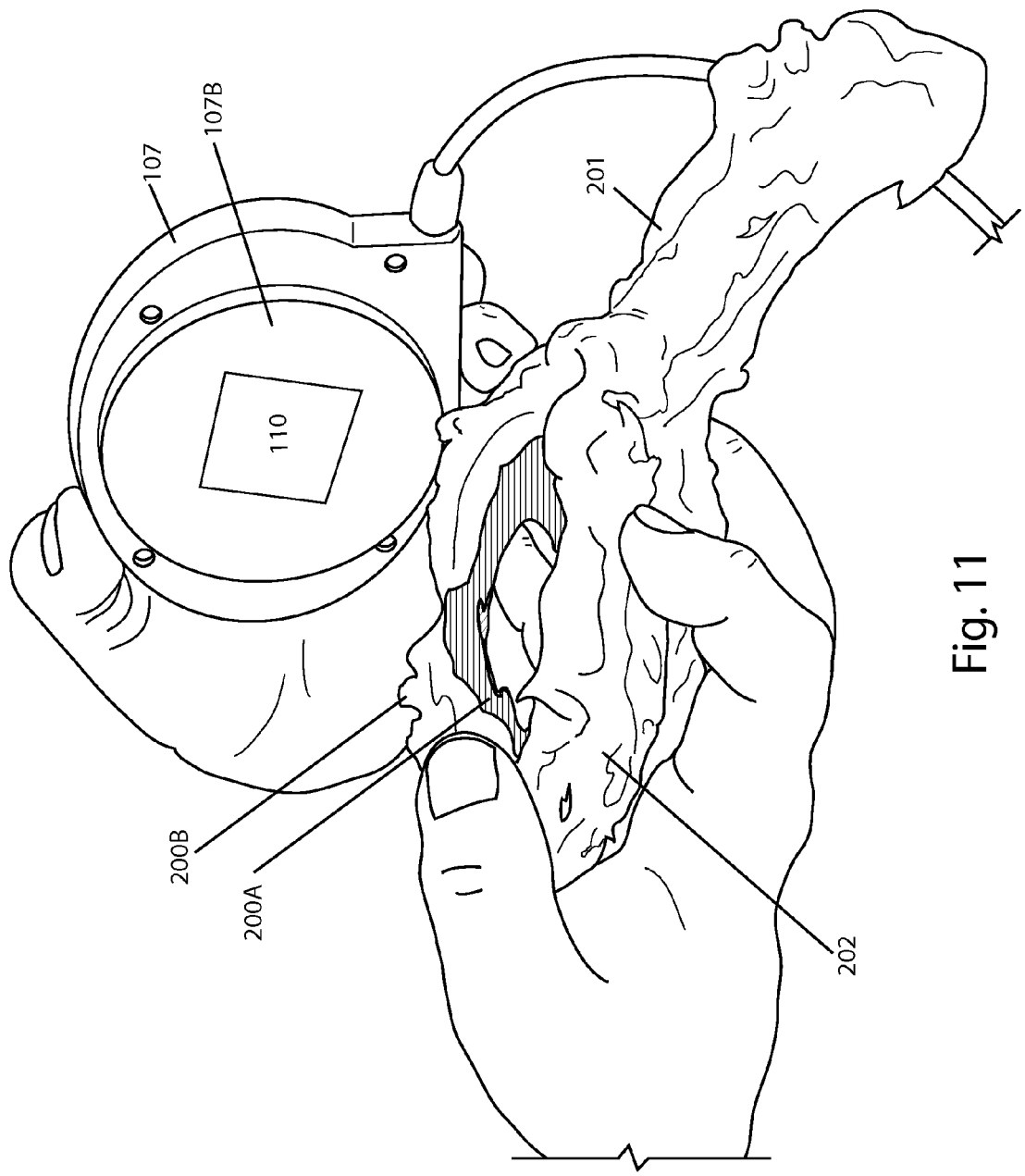
FIG. 11 is a top perspective view of a complete mold.

Referring next to FIG. 10 step five is shown, wherein a third layer of the moldable material 201 is applied over the embedded cable 106C, which is under the skin (see also FIG. 5). Thus, a support groove G (hidden) is formed in the moldable material 201 over the bulging 106C. This support groove G may be modified to fit over another protruding feature proximal to the location of the IMD such as a bone or other feature such as an ear. Referring next to FIG. 11 step six is shown showing all components of the antenna support 202 hardened. These components are designated 200A, 200B and 201. An optional step seven is shown adding a patch of double sided tape 110 to the bottom 107B of the external antenna 107.

Figure 12:
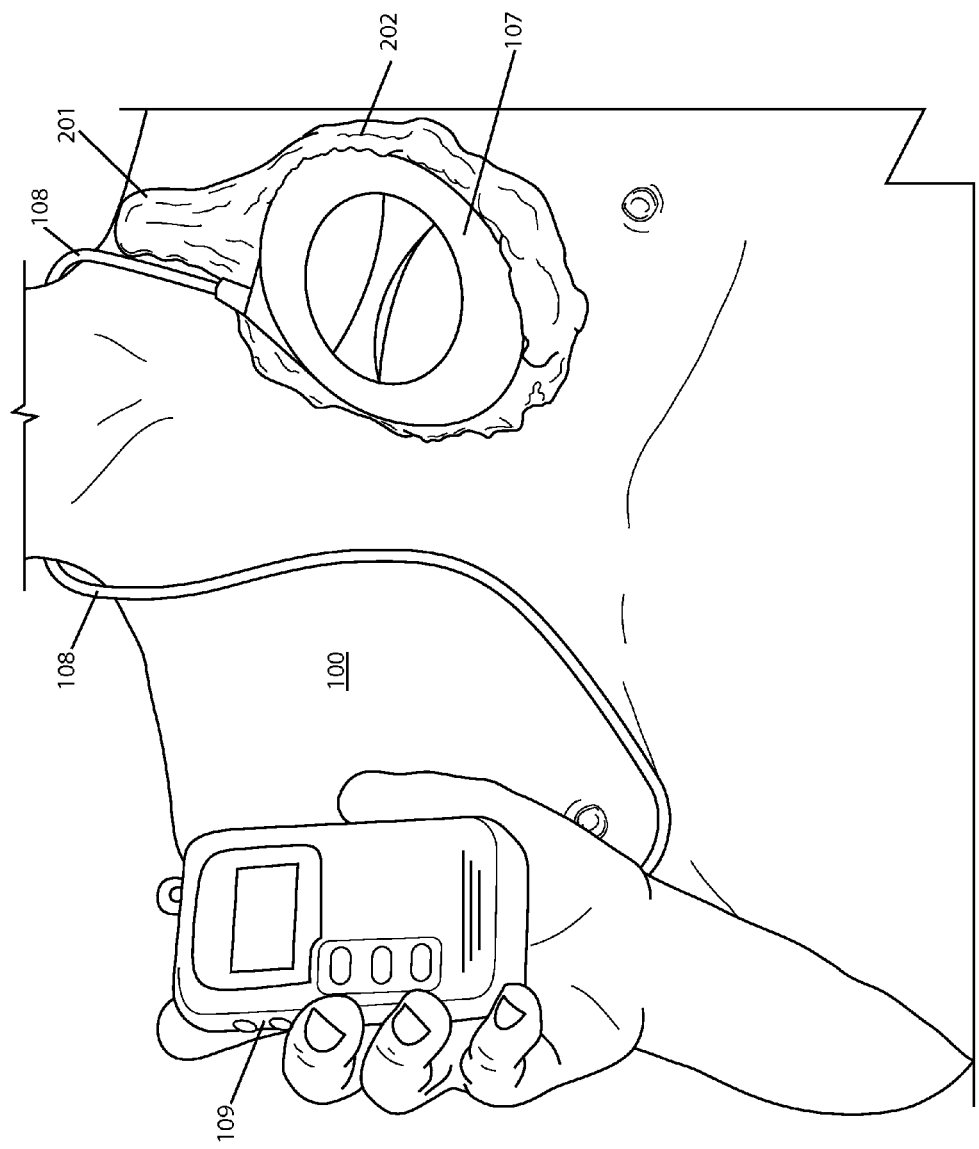
FIG. 12 is a front elevation view of a mold in operation showing a maximum charging signal.

Referring next to FIG. 12 the patient 100 is using the antenna support 202 in a sitting, but slightly reclining position to get a maximum charge from the charging unit 109. As indicated in Table 1 level IV, no other manipulation or support is needed for charging the unit in this position.

Figure 13:
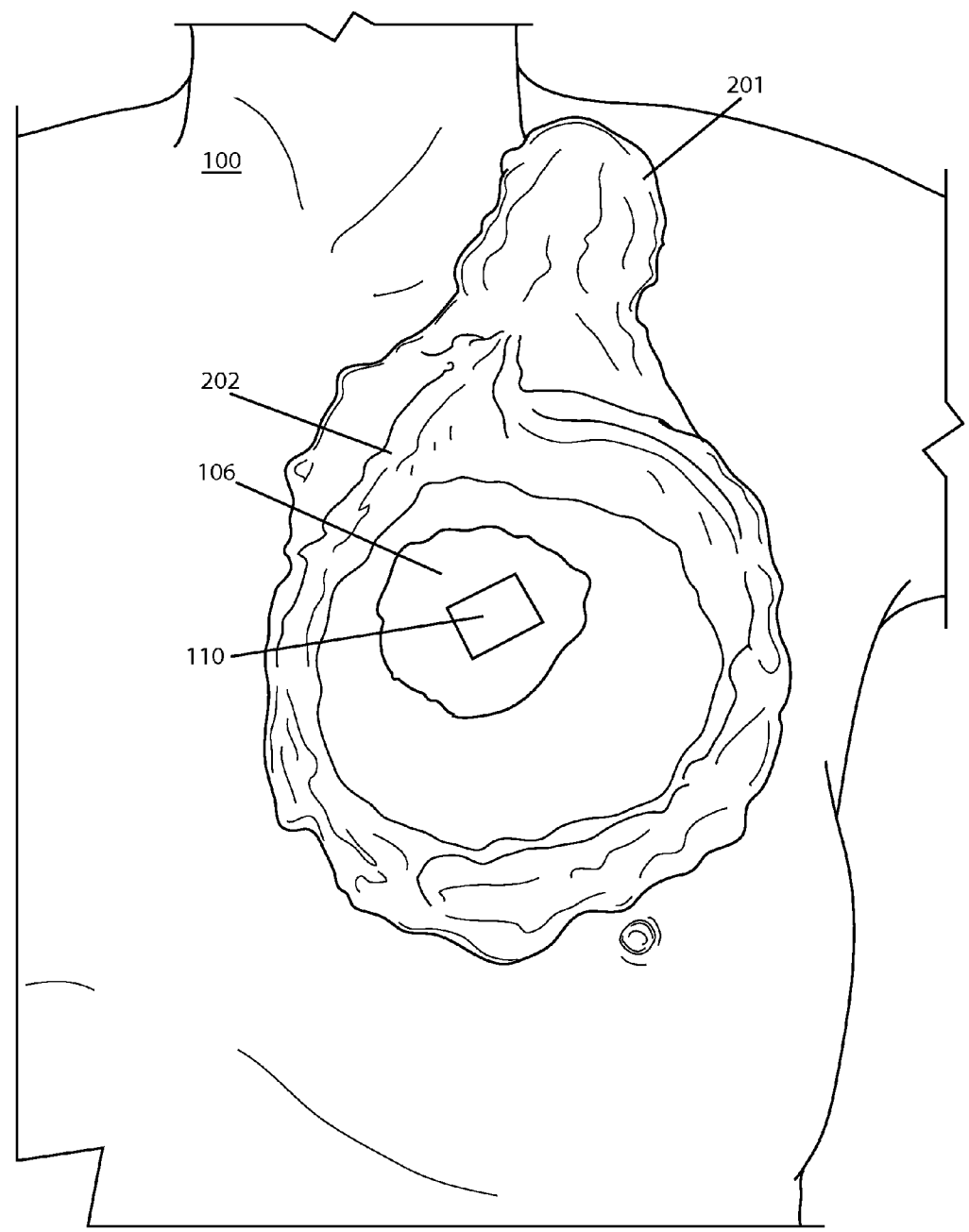
FIG. 13 is a front perspective view showing an additional optional step of adding a patch of two-sided tape to the RIMD surface on the patient's skin.

Referring next to FIG. 13, the patch 110 has been placed directly on the patient's skin 106 instead of on the bottom 107B of the charging antenna 107. This is a variation of optional step seven.

Figure 14:
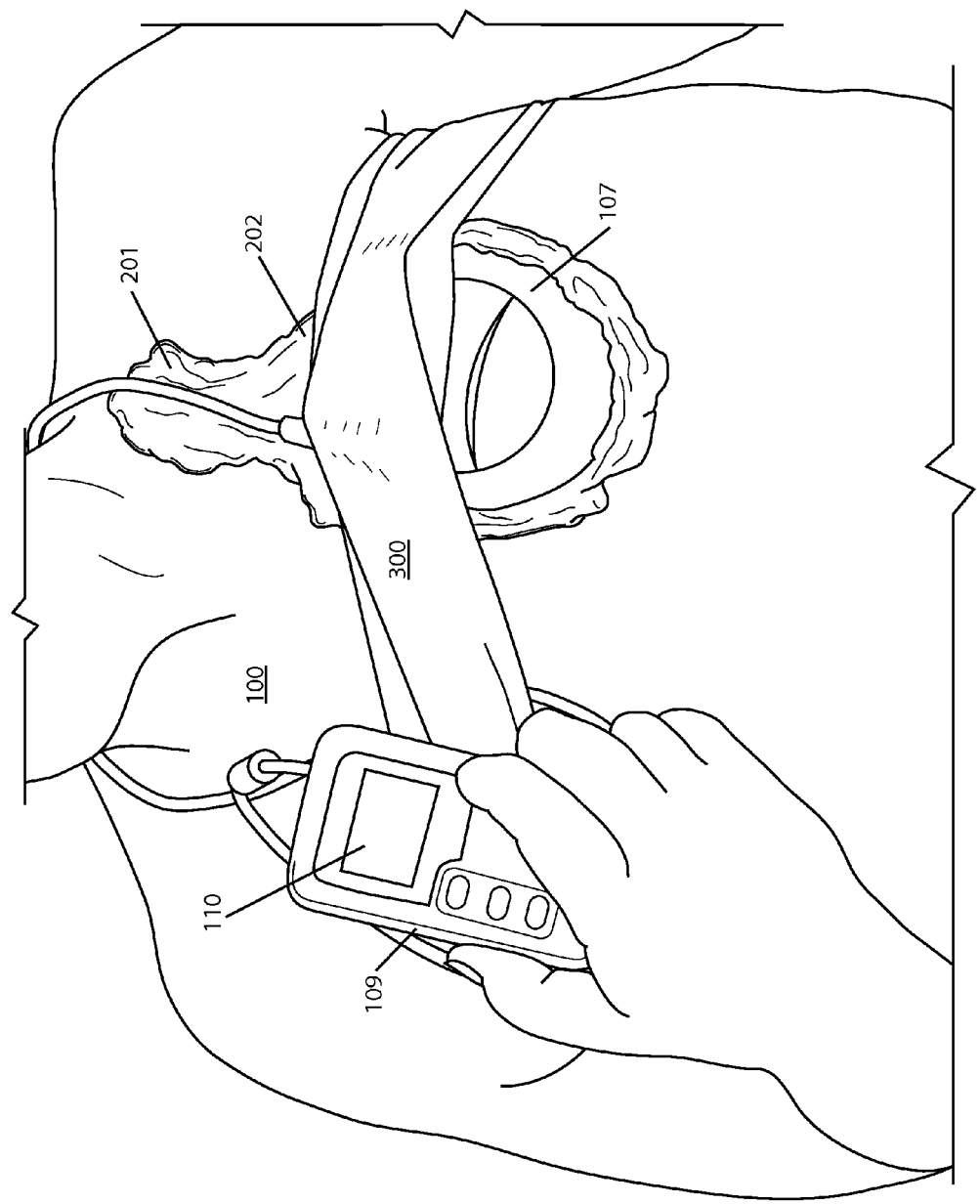
FIG. 14 is a front elevation view of an additional optional step of adding an elastic bandage wrap to secure the external antenna and mold in place.

Referring next to FIG. 14, an optional step eight is shown, wherein an elastic bandage 300 has been applied around the external antenna 107 that rests in the antenna support 202. This bandage 300 allows the patient 100 to move around while still getting a maximum efficiency from the charging unit 109.

Figure 15:
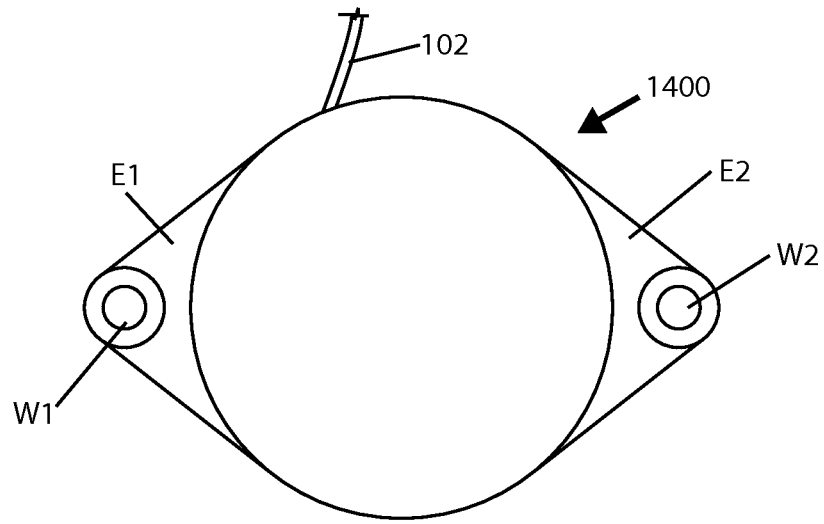
FIG. 15 is a front elevation view of an alternate embodiment metal ear RIMD.
Figure 16:
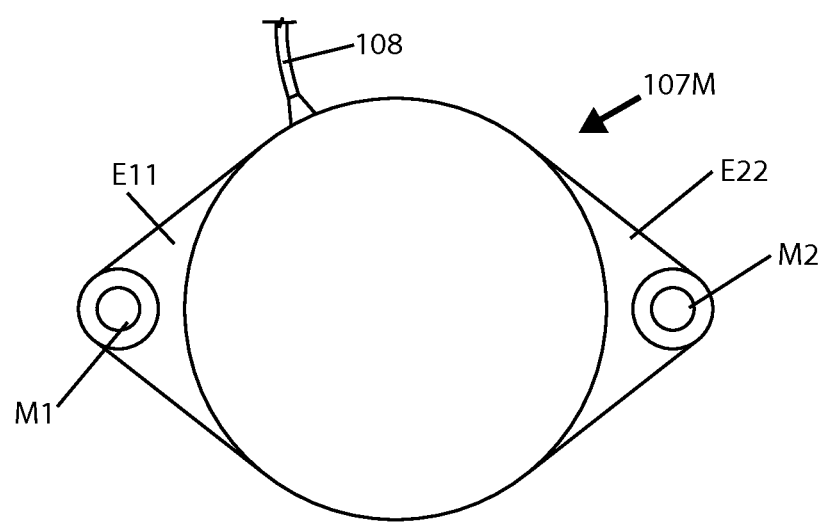
FIG. 16 is a front elevation view of an alternate embodiment magnetized ear external antenna.

Referring next to FIGS. 15, 16 an alternate embodiment using magnets is designated system 1400. This RIMD would have ears E1 and E2 protruding at opposing edges therefrom. Each ear E1, E2 has an iron metal disk or equivalent designated W1, W2. To avoid rusting a known coating has been applied over the iron or the iron has been encased in the titanium housing. An external antenna 107M has matching ears E11 and E22 which align with their respective embedded ears E1 and E2. Antenna ears E11 and E22 have been fitted with very strong rare earth magnets M1, M2. In operation these magnets M1, M2 support the external antenna 107M against the embedded ears E1, E2. A double-sided tape patch and/or an elastic bandage as noted above could be added to this system 1400. RIMD's implanted in other parts of the body may need a different shaped 201 segment of the antenna support or no 201 at all.

Figure 17:
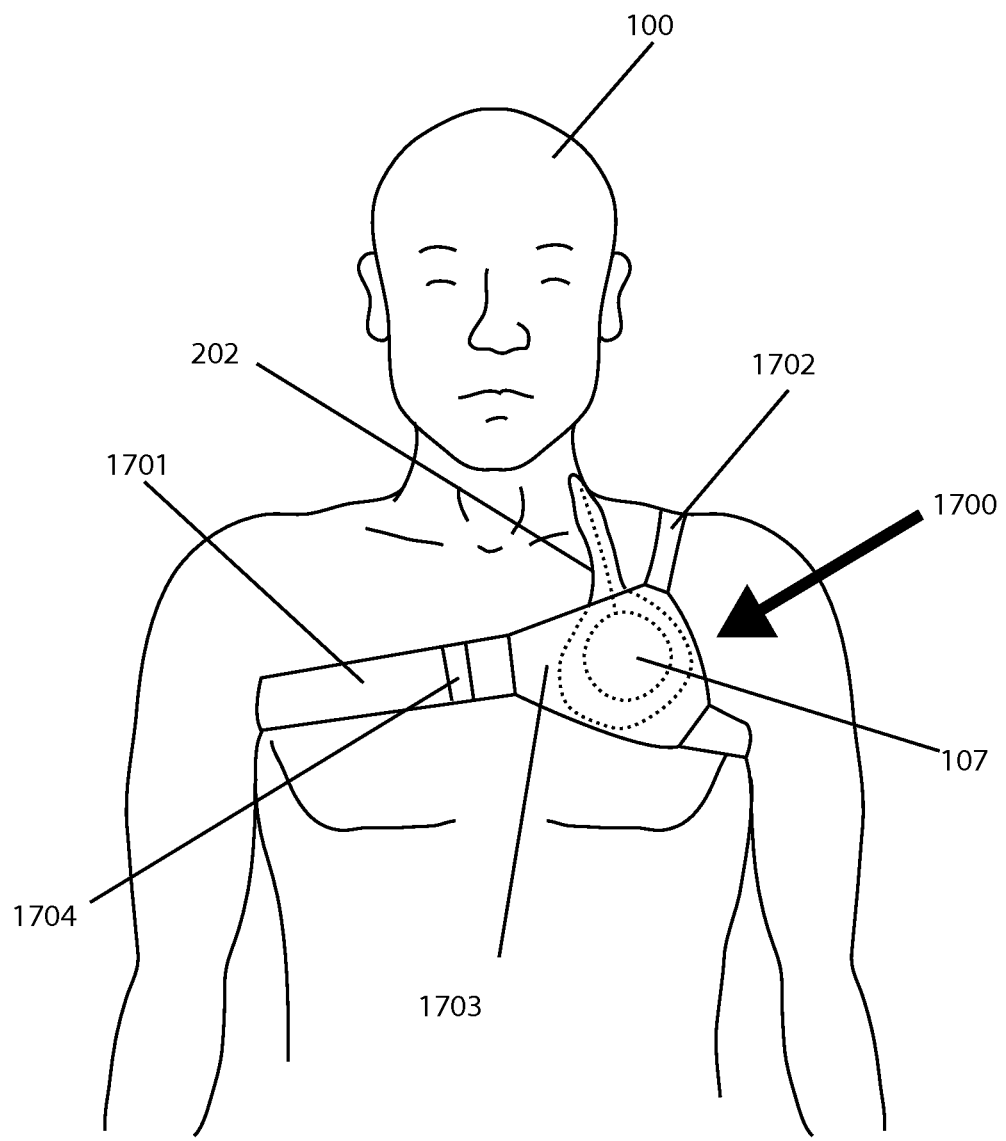
FIG. 17 is a front elevation view of an elastic harness embodiment.
Figure 18:
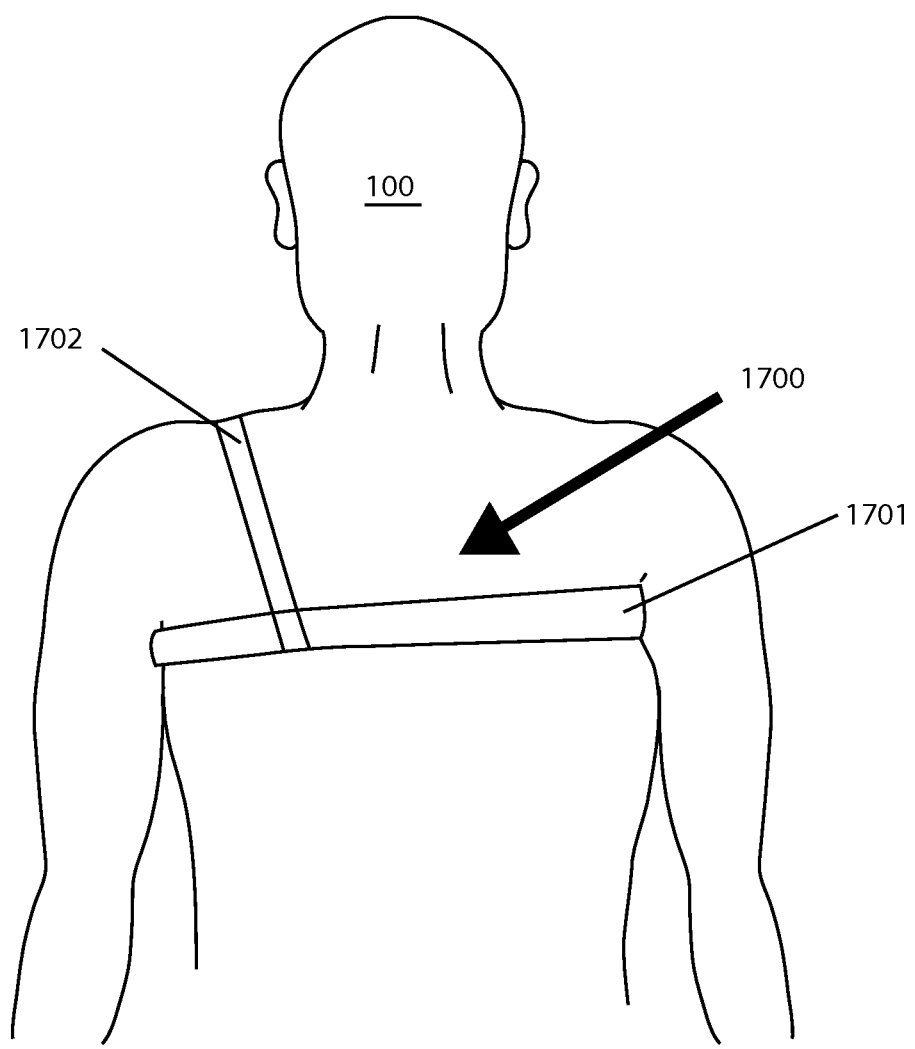
FIG. 18 is a rear elevation view of the elastic harness embodiment.

Referring next to FIGS. 17, 18 a special elastic harness 1700 has been made to support the antenna support 202 and the antenna 107. An elastic chest strap 1701 has a fastener 1704. The elastic chest strap 1701 has a cup 1703 that supports the antenna support 202 and the antenna 107. An elastic shoulder strap 1702 supports the cup 1703. In use the charging unit 109 could be tucked under the chest strap 1701. This elastic harness 1700 helps provide for patient mobility during charging.

Although the present invention has been described with reference to the disclosed embodiments, numerous modifications and variations can be made and still the result will come within the scope of the invention. No limitation with respect to the specific embodiments disclosed herein is intended or should be inferred. Each apparatus embodiment described herein has numerous equivalents.

I claim:

1. A method to efficiently charge a surgically implanted medical device (IMD) which is under the skin of a patient, the method comprising the steps of:
   a. applying a first layer of moldable material on an outer skin surface around the perimeter of the location of the IMD;
   b. placing an object with a flat surface on top of the first layer of moldable material so as to create a top level surface on the first layer of moldable material;
   c. allowing the first layer of moldable material to set;
   d. placing an external charging antenna on the first layer of molded material in an optimum position for charging the IMD;
   e. applying a second layer of moldable material around the external charging antenna and allowing the second layer of moldable material to set to form a unique molded cast around the external charging antenna; and
   f. allowing the external charging antenna to rest in the unique molded cast until the IMD is charged the desired amount.

2. The method of claim 1 further comprising the step of reclining the patient back at an angle between about 5° and about 70° from an upright seated position during charging.

3. The method of claim 1 further comprising the step of further securing the external charging antenna in the unique molded cast with an elastic or an adhesive member.

4. The method of claim 1 further comprising the step of applying a third layer of moldable material in contact with said second and/or first layer of moldable material and extending over or around an anchor point on the patient's body and allowing the third layer of moldable material to set to form a unique molded cast.

5. The method of claim 4, wherein the anchor point is a clavicle bone.

6. The method of claim 4, wherein the anchor point is an ear.

7. The method of claim 4, wherein the anchor point is a subcutaneous cable.

8. A method to efficiently charge an implanted battery operated medical device (IMD) which is surgically implanted under the skin so as to form a bulging target area above a normal skin surface area, the method comprising the steps of:
   a. applying a first layer of moldable material around the bulging target area;

b. placing a flat plate on top of the applied moldable material so as to create a level surface on the same plane as the bulging target area;
c. placing an external charging antenna on the formed molded layer in an optimum position for charging the implanted battery operated medical device;
d. applying a second layer of moldable material on top of the first layer of moldable material and around the external charging antenna to form a unique molded cast;
e. stabilizing the external charging antenna with the unique molded cast in an optimum position for charging the implanted battery operated medical device; and
f. allowing the external charging antenna to rest in the unique molded cast until the IMD is charged the desired amount.

9. The method of claim 8 further comprising applying a third layer of moldable material in contact with said second and/or first layer of moldable material and extending over or around an anchor point on the patient's body.

10. The method of claim 9, wherein the anchor point is a clavicle bone.

11. The method of claim 9, wherein the anchor point is an ear.

12. The method of claim 8 further comprising using an attachment device to further secure the external charging antenna to the skin and/or to the unique molded cast.

13. The method of claim 8 further comprising using at least one elastic fabric strip to secure the external charging antenna and unique molded cast to a patient's chest.

14. The method of claim 8 further comprising the step of using two elastic fabric strips, one around the chest, and a second over a shoulder, to further secure the external charging antenna and the unique molded cast.

15. The method of claim 8 further comprising the steps of using magnets in the implanted medical device and the external charging antenna.

* * * * *